United States Patent
Le

(10) Patent No.: US 10,899,676 B2
(45) Date of Patent: *Jan. 26, 2021

(54) ANIMAL FEED STOCK USING MICROBIAL ENHANCEMENT

(71) Applicant: Khanh Le, San Jose, CA (US)

(72) Inventor: Khanh Le, San Jose, CA (US)

(73) Assignee: Cisbay Global Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/693,290

(22) Filed: Nov. 23, 2019

(65) Prior Publication Data

US 2020/0189988 A1    Jun. 18, 2020

Related U.S. Application Data

(63) Continuation-in-part of application No. 15/405,247, filed on Jan. 12, 2017, now Pat. No. 10,524,487.

(51) Int. Cl.

| | |
|---|---|
| *C05F 3/00* | (2006.01) |
| *A23K 10/18* | (2016.01) |
| *A23K 10/37* | (2016.01) |
| *A23K 10/30* | (2016.01) |
| *A01K 5/00* | (2006.01) |
| *A23K 50/10* | (2016.01) |
| *A23K 50/75* | (2016.01) |
| *A23K 50/80* | (2016.01) |
| *A23K 50/30* | (2016.01) |
| *A23K 20/24* | (2016.01) |

(52) U.S. Cl.
CPC ............ *C05F 3/00* (2013.01); *A01K 5/008* (2013.01); *A23K 10/18* (2016.05); *A23K 10/30* (2016.05); *A23K 10/37* (2016.05); *A23K 20/24* (2016.05); *A23K 50/10* (2016.05); *A23K 50/30* (2016.05); *A23K 50/75* (2016.05); *A23K 50/80* (2016.05)

(58) Field of Classification Search
CPC ........ A23L 33/18; A23L 33/17; A23L 33/175; A23L 2/66; A23L 33/195; A23L 33/30; A23L 33/40; A61P 31/06; A61P 35/00; A61P 21/00; A61P 19/10; A61P 1/16; A61P 21/06; A61P 29/00; A61P 31/14; A61P 31/18; A61P 35/02; A61P 35/04; A61P 37/00; A61P 37/06; A61P 3/02; A61P 3/04; A61P 3/10; A61P 43/00; A61P 9/10; A61P 31/04; A61P 31/00; A23V 2002/00; A23V 2200/316; A23V 2250/06; A23V 2250/55; A61K 38/168; A61K 38/17; A61K 9/0053; A61K 38/00; A61K 38/10; A61K 38/16; A61K 38/164; A61K 38/1703; A61K 38/1709; A61K 38/1767; A61K 38/38; A61K 38/45; A61K 45/06; A61K 9/0075; A61K 9/0095; A61K 9/146; A61K 9/2054; A61K 9/2866; A61K 2039/5158; A61K 2039/55505; A61K 2039/55566; A61K 2039/6006; A61K 39/0011; A61K 39/0225; C12Y 207/04003; G01N 2500/00; G01N 33/6803; G01N 33/6806; G01N 33/6848; G01N 2800/06; G01N 33/53; G01N 33/66; G16B 20/00; C05F 3/00; C05F 11/08; A23K 10/18; A23K 10/37; A23K 20/24; A23K 50/10; A23K 50/30; A23K 50/75; A23K 50/80; A23K 10/30; A23K 50/60; C12N 2710/16122; C12N 2710/16222; C12N 15/111; C12N 15/1131; C12N 15/1132; C12N 2310/14; C12N 2320/11; C12N 2330/10; C12N 2740/16022; Y02A 40/20; Y02A 40/818; Y02A 90/10; Y02A 90/26; Y02E 50/30; Y02W 30/40; A01K 5/008; C05G 5/20; C05G 5/45; C05G 3/0052; C05G 3/0064; C07K 14/001; C07K 14/005; Y02P 20/145

See application file for complete search history.

(56) References Cited

U.S. PATENT DOCUMENTS

| | | | | |
|---|---|---|---|---|
| 3,719,327 | A * | 3/1973 | McMahan ............ | A01G 25/023 239/454 |
| 4,229,544 | A * | 10/1980 | Haynes .................... | C12N 1/04 435/252.1 |
| 4,952,229 | A * | 8/1990 | Muir ................... | A01G 13/0262 71/7 |
| 6,471,741 | B1 * | 10/2002 | Reinbergen ............ | A01N 63/00 71/6 |
| 6,951,643 | B2 * | 10/2005 | Rehberger ............... | C12N 1/20 424/780 |
| 2005/0287283 | A1 * | 12/2005 | Dicks ..................... | A23K 10/12 426/635 |
| 2008/0213865 | A1 * | 9/2008 | Lai .......................... | C12N 1/16 435/252.9 |
| 2011/0281725 | A1 * | 11/2011 | Pullen ..................... | A01N 65/36 504/206 |
| 2013/0330308 | A1 * | 12/2013 | Millan ..................... | C12N 1/20 424/93.41 |
| 2014/0234524 | A1 * | 8/2014 | Parks ...................... | A23K 50/10 426/635 |
| 2015/0230499 | A1 * | 8/2015 | Ollagnier ................ | A23L 27/72 426/61 |
| 2016/0368831 | A1 * | 12/2016 | Bontchev ................ | C05F 11/00 |

* cited by examiner

Primary Examiner — Deborah K Ware
(74) Attorney, Agent, or Firm — Patent Law Office, PC; Bao Tran

(57) ABSTRACT

In one aspect, a method for feeding animals includes selecting a plurality of strains of sporulated living microbes and form a microbial solution; and applying the microbial solution to a carrier. In another aspect during use, the method includes feeding animals with the microbial infused carrier to deliver microbes to a gastrointestinal tract alive; and germinating the microbes in the digestive tract and stimulating local intestinal immunity with the microbes.

6 Claims, 3 Drawing Sheets

FIG. 1

| |
|---|
| Select a plurality of strains of sporulated living microbes and form a microbial solution (12); |
| Mix a carrier such as almond hulls or shells with the microbial solution (14); |
| Feed animals with the microbial infused carrier (16) |
| Microbes reaches gastrointestinal tract alive (18) |
| Germinate in upper digestive tract (20) |
| Stimulate local intestinal immunity (22) |

ANIMAL FEED STOCK USING MICROBIAL ENHANCEMENT

This application is related to Applications 15404202 entitled "MICROBIAL SOIL ENHANCEMENTS" and Ser. No. 15/404208 entitled "SYSTEMS AND METHODS FOR WATER REMEDIATION", now US Patent No. 10179744, all of which are filed concurrently herewith, and the contents of which are incorporated-by-reference.

BACKGROUND

The present invention relates to microbial enhancements for animal feeds.

World demand for animals and animal products is tremendous and continually growing. The U.S. cattle and dairy industries alone are billion dollar industries. They involve millions of head of cattle that consume billions of dollars of feed annually.

Today's farm animals nutrition are well understood base on essential needs of micro ingredients such as vitamins and minerals premixed into "compound feed" which include corn, soybeans, sorghum, oats, and barley, in addition with chemical preservatives and antibiotics.

The use of antibiotics in animal feeds may lead to some of those drugs that may pass into meat, milk, eggs and other products with toxins that are harmful to humans. In the last few years probiotics have constantly increased in importance and aroused growing interest in animal nutrition.

SUMMARY OF THE INVENTION

In one aspect, a method for feeding animals includes selecting a plurality of strains of sporulated living microbes and form a microbial solution; and infusing a carrier with the microbial solution. In another aspect during use, the method includes feeding animals with the microbial infused carrier to deliver microbes to a gastrointestinal tract alive; and germinating the microbes in the digestive tract and stimulating local intestinal immunity with the microbes.

In a further aspect, a method for feeding animals includes selecting a plurality of strains of sporulated living microbes and form a microbial solution; infusing a carrier such as hulls or shells with the microbial solution; feeding animals with the microbial infused carrier and delivering microbes to a gastrointestinal tract alive; and germinating the microbes in the digestive tract and stimulating local intestinal immunity with the microbes.

In yet another aspect, a method for feeding animals includes selecting a plurality of strains of sporulated living microbes and form a microbial solution; selecting as a carrier for a predetermined animal:
 for grazing animal, one of hull, wheat, and dendritic salt,
 for poultry, dendritic salt or calcium carbonate,
 for aquatic animal, dendritic salt;
 for swine, dendritic salt or calcium carbonate.
The microbial solution is then applied to the carrier.

Implementations of the above aspects may include one or more of the following. The microbes can be selected from Bacillus (B.) acidiceler, B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a. subsp. amyloliquefaciens, B. a. subsp. plantarum, B. amylolyticus, B. andreesenii, B. aneurinilyticus, B. anthracia, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g. subsp. globisporus, B. g. subsp. marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizospharae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s. subsp. inaquosorum, B. s. subsp. spizizenii, B. s. subsp. subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis, and B. zhanjiangensis.

Advantages of the solutions may include one or more of the following. One embodiment called PROBIOFEED provides a natural and unique blend of specifically selected beneficial bacteria & probiotic additives to promote well-being of animals by preventing bacteria and parasitic contamination. Beneficial bacteria are essential to all life, PROBIOFEED will enhance the animals immunity, improving digestibility, improve intestinal health, increase animal survival rate and resistance to bad pathogen and diseases. More importantly, PROBIOFEED promotes animal growth and feed efficiency, which will add to a farmer's bottom line.

These and other advantages are achieved by the present invention, which provides a method of preserving and solutions containing microbial spores and/or colonies.

BRIEF DESCRIPTION OF THE FIGURES

FIG. 1 shows an exemplary process to infuse hulls or shells with microbials for feeding animals.

DETAILED DESCRIPTION OF THE INVENTION

Figure 2A:
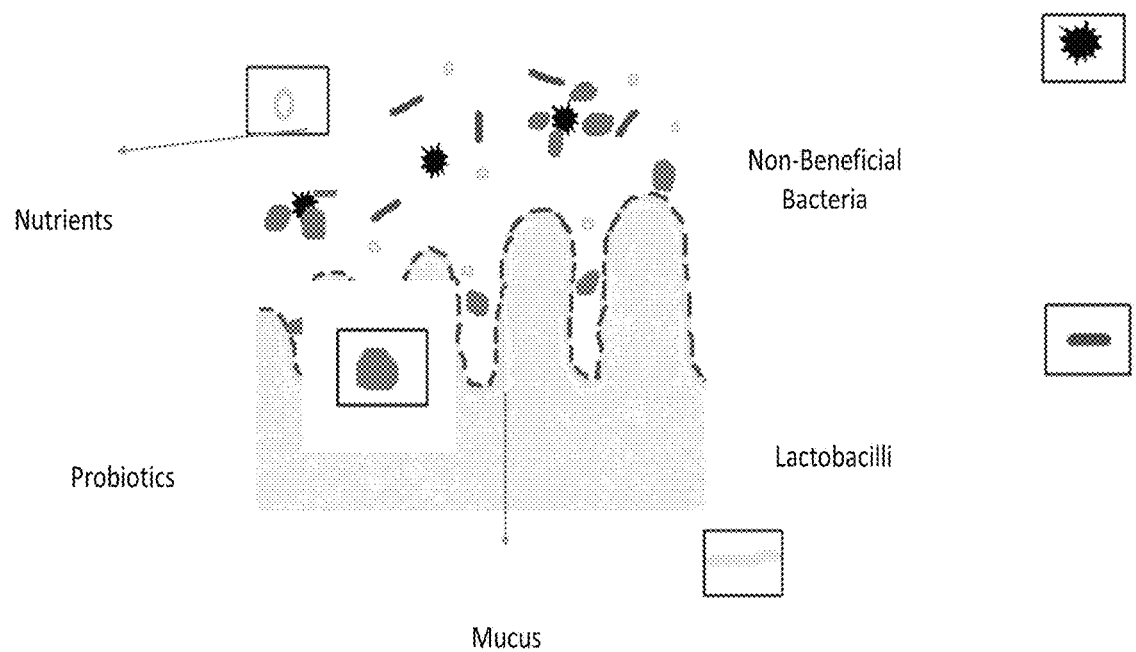
FIG. 2A shows an exemplary digestive tract with nutrients, non-beneficial bacteria, lactobacilli and probiotics.

FIG. 1 shows an exemplary process to infuse hulls or shells with microbials for feeding animals. The process includes:
Select a plurality of strains of sporulated living microbes and form a microbial solution (12);
Infuse a carrier such as hulls or shells with the microbial solution (14);
Feed animals with the microbial infused hulls or shells (16)
Microbes reaches gastrointestinal tract alive (18)
Germinate in upper digestive tract (20)
Stimulate local intestinal immunity with the microbes (22)

Different carriers can be used. Beside hulls, the feed can use wheat or corn powder for carrier. Dendritic salt and grind up limestone or calcium carbonate can be used as well. The purpose of using salt as a carrier is to help the animal restore electrolytes in the body. This problem is often caused by extreme heat in the summer, mineral deficiency in winter and after severe diarrhea. The salt will not only help retain water, electrolytes in the body, but also increases appetite. Wheat, hull, corn carriers provide more nutrients in the diet but should be used when the animal is healthy during a normal growing cycle. For example, grazing animals, the feed includes hull, wheat, and dendritic salt for the carrier, depending on the season. For poultry, the feed includes dendritic salt or calcium carbonate. For aquatic fish and other creatures, dendritic salt is used. For swine, the feed can include dendritic salt or calcium carbonate.

In one embodiment called PROBIOFEED, the solution contains several strains of bacillus spp to ensure a broad spectrum product that can work in wide variety of environmental applications. The Bacillus spp germinates in upper digestive tract and display their activity in those sections of intestine which are relevant for nutrient absorption. Bacillus is selected as a sporulated living microorganism with the ability to form spores. They reach the gastrointestinal tract alive and stimulates local intestinal immunity.

Various cell walls that protect the nucleus from external stresses enable the Bacillus products to withstand massive stress during feed production and storage caused by 1) High temperature, 2) Pressure, 3) Shear forces, and 4) Oxidation impacts. In some embodiments, selected cell walls are used as a protective structure/mechanism for producing the Bacillus included products.

Figure 2B:
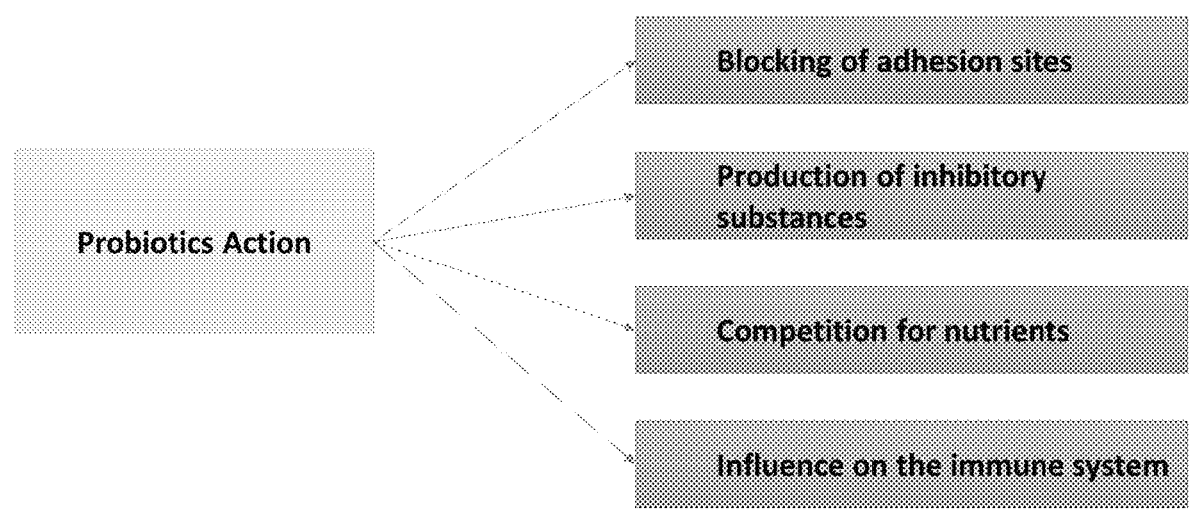
FIG. 2B shows exemplary probiotics actions.

FIG. 2A shows an exemplary digestive tract with nutrients, non-beneficial bacteria, lactobacilli and probiotics. As detailed in FIG. 2B, probiotics actions include: blocking of adhesion sites, production of inhibitory substances, competition for nutrients, and influencing the immunity system. The benefits include improved digestibility of nutrients and detoxification of toxic molecules and improved vitamin synthesis (B and K). This provides an environmental friendly animal husbandry.

The probiotics provide antagonistic action against non-desirable microorganisms (barrier effect) and protects the intestinal mucous membrane against invading microorganisms. They contribute to maturation and stimulation of the host's immune system; improve growth and survivability of the animal; and reduce feed cost. The probiotics also improve feed conversion (FCR), decrease by 1%-5% and improves daily weight gain (DWG), increase by 3%-5%. Yet other benefits include one or more of the following:
Increased production and survivability
Reduced risk of digestive problems
Improved nutrients absorption
Uniform growth and better homogeneity of the groups
Reduced fattening period
Reduced feed expenditure
Reduced medication costs
Reduced slurry nutrient content (lower nitrogen excretion for example)

Next, exemplary results on probiotics on the performance of animals are shown as follows:

| Influence of various probiotics on the performance of animals | | |
|---|---|---|
| Production branch | DWG (% of control) | FCR (% of control) |
| Piglet production | +4.8 | −1.5 |
| | (−8.1 to +24.3) | (+3.1 to −9.3) |
| Calf production | +5.4 | −2.5 |
| | (−5.3 to +21.7) | (+3.6 to −7.9) |
| Growing/fattening pigs | +3.7 | −5.1 |
| | (−0.3 to +6.7) | (−1.4 to −7.1) |
| Growing/fattening cattle | +3.4 | −2.7 |
| | (−4.3 to +7.2) | (+7.6 to −4.7) |

| influence of probiotics on protein digestibility and crude protein deposition in piglets | | | | |
|---|---|---|---|---|
| Nitrogen digestibility (%) | | Nitrogen deposition (g $W^{-0.75}$ per day)[1] | | |
| Control | Probiotic* | Control | Probiotic** | Authors |
| 81.05$^a$ | 85.86$^b$ | 1.24$^a$ | 1.34$^b$ | S E Scheuermann, 1993 |
| 78.70$^c$ | 83.20$^d$ | 1.76 | 1.81 | Tossenberger al., 1995 |

[1]Relative to metabolic body weight
**dosage 1 × 10$^9$ CFU per kg of piglet feed
$a,b,c,d$significant differences To feed the animals, in various embodiments:
For feed blending as a pre-mixed or coating: about 0.5 gram per kilogram of feed
For per feed mixing (can be mixed to one meal per day): about 2 grams per kilogram of feed
For drinking dosage: about 2 grams per liter of water.

The microbes used for animal nutrition have a very good safety record. Even in cases of overdoses of more than thousand times recommended levels in feed, there're no signs of dysbiosis in the gastrointestinal tract. Probiotics do not constitute any health hazard for animal. Since they are not transferred from intestine into the body of animal, probiotics do not affect any metabolic processes, nor do they have any negative impact on the animal.

Figure 3:
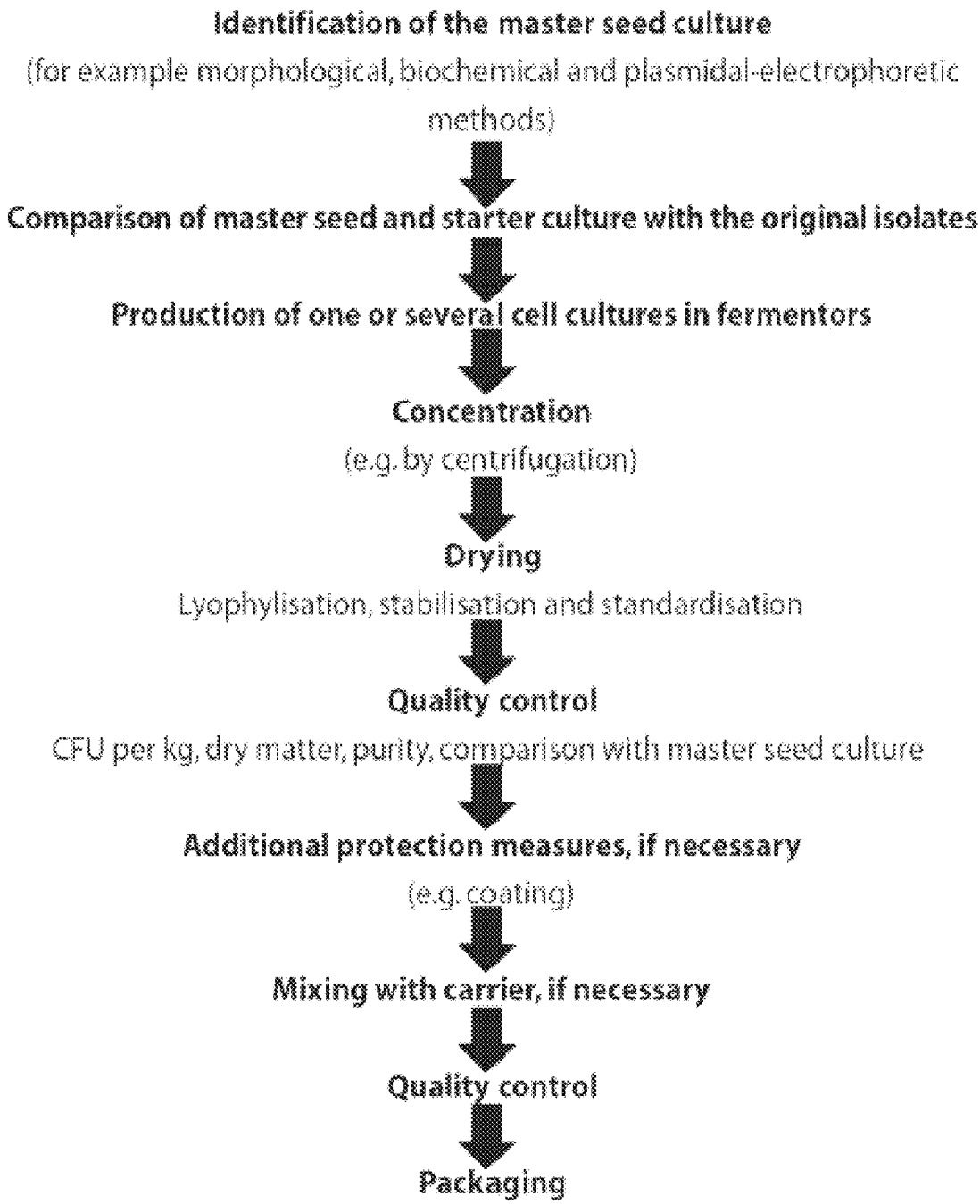
FIG. 3 shows an exemplary process to form PROBIOFEED.

FIG. 3 shows an exemplary process to form PROBIO-FEED. First, the master seed culture is identified. Next, the process compares the master seed and starter culture with the original isolates. One or more cell cultures are produced in fermenters, and the result can be concentrated by centrifugation, among others. The concentrated cell cultures can be dried using lyophilisation, stabilization, and standardization techniques. Quality control is then done and the result can be compared with the master seed culture. Additional protection measures can be applied, such as coating the dried cell cultures. The result can be mixed with a carrier if necessary, and then quality control can be done. The resulting PROBIOFEED composition can be packaged for shipping. PRO BIOFEED Final Packaging can include Bags/Buckets/Drums, among others.

Various exemplary microbial compositions are detailed next.

EXAMPLE 1

Microbes:
*Bacillus pumilus* 4.05×10^8 CFU/g
*Bacillus subtilis* 6.30×10^8 CFU/g
*Bacillus amyloliquefaciens* 5.85×10^8 CFU/g
*Bacillus lichniformis* 1.80×10^8 CFU/g
Amino Acids: Amino Acids
Dendritic Salt: Sodium Chloride

EXAMPLE 2

Microbes:
*Bacillus licheniformis* 2.28×10^9 CFU/g
*Bacillus subtilis* 2.28×10^9 CFU/g
Dendritic Salt: Sodium Chloride

EXAMPLE 3

Microbes:
*Bacillus licheniformis* 4.762×10^9 CFU/g
Amino Acids: Amino Acids
Ground Lime Stone: Calcium Carbonate

EXAMPLE 4

Microbes:
*Bacillus licheniformis* 2.28×10^9 CFU/g
*Bacillus subtilis* 2.28×10^9 CFU/g
Almond Hull: Ground Almond Hull

EXAMPLE 5

Microbes:
*Bacillus licheniformis* 4.762×10^9 CFU/g
Amino Acids: Amino Acids
Dendritic Salt: Sodium Chloride

EXAMPLE 6

Microbes:
*Bacillus Subtilis* 4.762×10^9 CFU/g
Amino Acids: Amino Acids
Dendritic Salt: Sodium Chloride In another aspect, a method for enhancing soil in a predetermined farming area includes selecting a plurality of strains of sporulated living microbes and form a microbial solution; infusing the microbes with a carrier for a predetermined animal; feeding the animal with the microbes infused carrier; excrementing the microbes infused carrier as the animal moves around the area to receive the soil enhancement; and upon receipt of liquid, activating the microbes to perform soil enhancement.

In yet another aspect, an apparatus includes a container for a carrier selected based on a predetermined animal:
  for grazing animal, one of hull, wheat, and dendritic salt,
  for poultry, dendritic salt or calcium carbonate,
  for aquatic animal, dendritic salt;
  for swine, dendritic salt or calcium carbonate; and
  a microbial container housing a microbial solution with a plurality of strains of sporulated living microbes, wherein the microbial solution is applied to the carrier to form animal food; and a source of liquid to activate the microbes after excretion.

In a further aspect, a method for feeding animals includes selecting a plurality of strains of sporulated living microbes and form a microbial solution; infusing a carrier such as hulls or shells with the microbial solution; feeding animals with the microbial infused carrier and delivering microbes to a gastrointestinal tract alive; and germinating the microbes in the digestive tract and stimulating local intestinal immunity with the microbes. In yet another aspect, a method for feeding animals includes selecting a plurality of strains of sporulated living microbes and form a microbial solution; and selecting as a carrier for a predetermined animal:
  for grazing animal, one of hull, wheat, and dendritic salt,
  for poultry, dendritic salt or calcium carbonate,
  for aquatic animal, dendritic salt;
  for swine, dendritic salt or calcium carbonate.

The microbial solution is then applied to the carrier.

Implementations of the above aspects may include one or more of the following. The microbes can be selected from *Bacillus (B.) acidiceler,B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a. subsp. amyloliquefaciens, B. a. subsp. plantarum, B. amylolyticus, B. andreesenii, B. aneurinilyticus, B. anthracia, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B.*

*enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g. subsp. globisporus, B. g. subsp. marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s. subsp. inaquosorum, B. s. subsp. spizizenii, B. s. subsp. subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis, and B. zhanjiangensis.*

Advantages of the solutions may include one or more of the following. The technique simultaneously feeds animals AND fertilizes the land. This is done without any complicated equipment selection done by the prior art. Cost is low, and the result is environmentally sustainable. One embodiment called PROBIOFEED provides a natural and unique blend of specifically selected beneficial bacteria & probiotic additives to promote wellbeing of animals by preventing bacteria and parasitic contamination. Beneficial bacteria are essential to all life, PROBIOFEED will enhance the animals immunity, improving digestibility, improve intestinal health, increase animal survival rate and resistance to bad pathogen and diseases. More importantly, PROBIOFEED promotes animal growth and feed efficiency, which will add to a farmer's bottom line.

These and other advantages are achieved by the present invention, which provides a method of preserving and solutions containing microbial spores and/or colonies.

An exemplary process to naturally enhance soils without machinery can be done by providing microbes as part of the feed and as the animal such as cow moves around the planting area, the animal excrete the microbes into the soil which is subsequently activated with a liquid such as water. The process includes:

Select a plurality of strains of sporulated living microbes and form a microbial solution (12);

Mix a carrier such as almond hulls or shells with the microbial solution (14);

Feed animals with the microbial infused carrier (16)

Animal excrements carrier with microbial soil enhancement during natural grazing movements over various spots on the land to be soil enhanced (18)

Microbial infused carrier is dormant until receiving predetermined liquid amount (20)

Microbes are activated to enhance soil (22)

Different carriers can be used. Beside hulls, the feed can use wheat or corn powder for carrier. Dendritic salt and grind up limestone or calcium carbonate can be used as well. The purpose of using salt as a carrier is to help the animal restore electrolytes in the body. This problem is often caused by extreme heat in the summer, mineral deficiency in winter and after severe diarrhea. The salt will not only help retain water, electrolytes in the body, but also increases appetite. Wheat, hull, corn carriers provide more nutrients in the diet but should be used when the animal is healthy during a normal growing cycle. For example, grazing animals, the feed includes hull, wheat, and dendritic salt for the carrier, depending on the season. For poultry, the feed includes dendritic salt or calcium carbonate. For aquatic fish and other creatures, dendritic salt is used. For swine, the feed can include dendritic salt or calcium carbonate.

In one embodiment called PROBIOFEED, the solution contains several strains of bacillus spp to ensure a broad spectrum product that can work in wide variety of environmental applications. The *Bacillus spp* germinates in upper digestive tract and display their activity in those sections of intestine which are relevant for nutrient absorption. *Bacillus* is selected as a sporulated living microorganism with the ability to form spores. They reach the gastrointestinal tract alive and stimulates local intestinal immunity.

Various cell walls that protect the nucleus from external stresses enable the Bacillus products to withstand massive stress during feed production and storage caused by 1) High temperature, 2) Pressure, 3) Shear forces, and 4) Oxidation impacts. In some embodiments, selected cell walls are used as a protective structure/mechanism for producing the *Bacillus* included products. FIG. 2A shows an exemplary digestive tract with nutrients, non-beneficial bacteria, lactobacilli and probiotics. As detailed in FIG. 2B, probiotics actions include: blocking of adhesion sites, production of inhibitory substances, competition for nutrients, and influencing the immunity system. The benefits include improved digestibility of nutrients and detoxification of toxic molecules and improved vitamin synthesis (B and K). This provides an environmental friendly animal husbandry.

The probiotics provide antagonistic action against non-desirable microorganisms (barrier effect) and protects the intestinal mucous membrane against invading microorganisms. They contribute to maturation and stimulation of the host's immune system; improve growth and survivability of the animal; and reduce feed cost. The probiotics also improve feed conversion (FCR), decrease by 1%-5% and improves daily weight gain (DWG), increase by 3%-5%. Yet other benefits include one or more of the following:

- Increased production and survivability
- Reduced risk of digestive problems
- Improved nutrients absorption
- Uniform growth and better homogeneity of the groups
- Reduced fattening period
- Reduced feed expenditure
- Reduced medication costs
- Reduced slurry nutrient content (lower nitrogen excretion for example)

Next, exemplary results on probiotics on the performance of animals are detailed. To feed the animals, in various embodiments:

- For feed blending as a pre-mixed or coating: about 0.5 gram per kilogram of feed
- For per feed mixing (can be mixed to one meal per day): about 2 grams per kilogram of feed
- For drinking dosage: about 2 grams per liter of water.

The microbes used for animal nutrition have a very good safety record. Even in cases of overdoses of more than thousand times recommended levels in feed, there're no signs of dysbiosis in the gastrointestinal tract. Probiotics do not constitute any health hazard for animal. Since they are not transferred from intestine into the body of animal, probiotics do not affect any metabolic processes, nor do they have any negative impact on the animal.

In another method, first, the master seed culture is identified. Next, the process compares the master seed and starter culture with the original isolates. One or more cell cultures are produced in fermenters, and the result can be concentrated by centrifugation, among others. The concentrated cell cultures can be dried using lyophilisation, stabilization, and standardization techniques. Quality control is then done and the result can be compared with the master seed culture. Additional protection measures can be applied, such as coating the dried cell cultures. The result can be mixed with a carrier if necessary, and then quality control can be done. The resulting PROBIOFEED composition can be packaged for shipping. PRO BIOFEED Final Packaging can include Bags/Buckets/Drums, among others. Various exemplary microbial compositions are detailed next.

EXAMPLE 1

Microbes:
Bacillus pumilus 4.05×10^8 CFU/g
Bacillus subtilis 6.30×10^8 CFU/g
Bacillus amyloliquefaciens 5.85×10^8 CFU/g
Bacillus lichniformis 1.80×10^8 CFU/g
Amino Acids: Amino Acids
Dendritic Salt: Sodium Chloride

EXAMPLE 2

Microbes:
Bacillus licheniformis 2.28×10^9 CFU/g
Bacillus subtilis 2.28×10^9 CFU/g
Dendritic Salt: Sodium Chloride

EXAMPLE 3

Microbes:
Bacillus licheniformis 4.762×10^9 CFU/g
Amino Acids: Amino Acids
Ground Lime Stone: Calcium Carbonate

EXAMPLE 4

Microbes:
Bacillus licheniformis 2.28×10^9 CFU/g
Bacillus subtilis 2.28×10^9 CFU/g
Almond Hull: Ground Almond Hull

EXAMPLE 5

Microbes:
Bacillus licheniformis 4.762×10^9 CFU/g
Amino Acids: Amino Acids
Dendritic Salt: Sodium Chloride

EXAMPLE 6

Microbes:
Bacillus Subtilis 4.762×10^9 CFU/g
Amino Acids: Amino Acids
Dendritic Salt: Sodium Chloride In one embodiment, a selectively bred microbial solution has multiple single microbial series separately cultivated and followed with cross cultivation among those microbial series in a specific sequence and contains each of those microbial series, and by-products produced by those crossly cultivated microbial series are used for applications in modifying soil quality, activating soil, effectively degrading soil pollution, and helping growth of crops in a soil enhancement embodiment. After the selective breeding through the fermentation, the selectively bred naturally-occurring microorganisms have the ability to penetrate through the soil while enriching with micronutrients, microbial cultures and organic materials in a highly concentrated stage.

To supplement soil, the process selects a microbial solution with predetermined characteristics for agriculture use. For example, the characteristics can focus on microbes that work on nitrogen fixing or production in the soil. Next, the process iteratively and selectively breeds generations of microbes for microbial strain selection with predetermined microbial gene profiles to arrive at a predetermined microbial solution in a highly concentrated form of at least $1\times10^7$ cfu/ml in one embodiment and in other embodiment of at least $1\times10^9$ cfu/ml. This process can be aided using DNA sequencing analysis to guide the production of the generations of microbes. The multiple single microbial series are separately cultivated and followed with cross cultivation among the microbial series in a specific sequence. Once the microbial population has arrived, the process mixes by-products produced by the crossly cultivated microbial series with humic acid and a filler such as kelp. Other additives such as fertilizer including PNK chemical can be added. The entire batch can be in liquid form, but preferably the water component is removed, leaving the pellets or solid products that can be planted into the soil.

Once implanted, the humic acid binds or attaches soil to the fertilizer and microbes. The microbes in turn help the plant to absorb the fertilizer and result in significant root growth, leading to plant growth. A major benefit is that the fertilizer is localized to the root due to the humic acid binding to minimize chemical runoffs, which pollute downstream water bodies, rivers, or lakes.

To selectively breed the microbes for agricultural use, fermentation media are prepared with a nutrient supply (1). The nutrients can include a carbon source Dextrose or Glucose. Additional carbon sources can be used with the dextrose or glucose singly or in combination. For example, another carbon source can be sucrose, for example. Next, a nitrogen source is provided such as soy protein that has not been genetically modified (2). Next, in (3), micronutrients—Calcium, Magnesium and Zinc are provided. A person of ordinary skilled in the art appreciates that various compositions of the fermentation media can be prepared so long as the nutrients, one or more of the carbon sources, and the micronutrients are included.

In (4), the fermentation media is prepared using water supply and sterilized using stream sterilizer at 120 degrees Celsius for 45 minutes, but the temperature and time can be varied in accordance with tank volume. In (5), the process produces the microbial products, as is detailed in FIG. 2. At each stage, quality control methods are applied using standard plate count method for *Shigella, E. Coli, Salmonella Yersinia* and *Psuedomonas beroginosa* for their absence. All products are manufactured according to USEPA (United States Environmental Protection Agency) standards.

The microbes can be: *Bacillus amyloliquefaciens* at $5.85 \times 10^{74}$ cfu/ml, *Bacillus licheniformis* at $1.80 \times 10^7$ cfu/ml, *Bacillus megaterium* $2.5 \times 10^8$ CFU/ml, *Bacillus pumilus* at $4.05 \times 10^7$ cfu/ml, or *Bacillus subtilis* at $6.30 \times 10^7$ cfu/ml. Leonardite and urea and water can be used with the microbes. Polyloxy—(1,2-Ethanedily), Alpha-(nonylphenyl)-omega-hydroxy can be used with the microbes. The solution can also include Leonardite and water.

The Microbial Strain selection and profile of microbial genes are carefully selected to form the formulation of products. Through strain selections, screening and improvement, the system generates various bio-fertilizer products for rejuvenating soil and promote plant growth. For example, *Bacillus Subtilus* has 4,100 genes. These genes each contain approximately 2000 traits. In turn, each one of these traits and its mutation has over 1000 profiles and sub-profiles.

With a member of *Bacillus* as the microbe, the process can include a carrier from one of: liquid, water, dry humic acid, wet humic acid, urea, soil wetting aid, or a penetrant. When applied in the field to plants, billions of the selectively bred bacteria operate to covert and breakdown organic matter into a form of micronutrient for plant uptake. The microbial solution can be applied through spraying, wetting, dipping, misting, drenching, showering, fogging, soaking, dampening, drizzling, dousing and splashing.

The biodiversity of *Bacillus* group and beneficial traits of *bacillus* species are useful in plant protection. *Bacillus* genus is widely spread in nature. *Bacillus* species such as *B. Subtilus, B. Megaterium, B. Amyloliquefaciens, B. lichniformis* are carefully selected, for their specific profile which contains beneficial traits for plant protection and growth promotion that comprise the synthesis in broad-spectrum with active metabolites and easily adaptation in various environment conditions that benefit plant bacterial interaction and advantageous of formulation process.

As plants roots exudates and lysates attract and stimulate microbial activity in the root surrounding soil, the zhizosphere (chemical space around the roots) became highly populated. Beneficial *Bacillus* spp. strains can compete with other bacteria and fungi that could adversely affect crops. They can inhibit phytopathogenic attacks such as "Basal Stem Rot, phytophthora, fusarium", or induce host-plant defense system against potential pathogenic attacks, stimulate plant growth, improve nutrient uptake, and reduce negative environment traits.

Beneficial traits with an agricultural purpose in *Bacillus Subtilis* and related species are detailed next. The species of bacillus group, particularly *B. Subtilus, B. Megaterium, B. Amyloliquefaciens, B. lichniformis* are extremely importance in agriculture, as phytopathogenic antagonist or plant growth promoters. It is often referring as "Plant Growth Promoting rhizobacteria" or PGPR. PGPR are naturally occurring soil bacteria that have the ability to colonize the roots, and the high concentration and the number of bacteria artificially created (added) as detailed above enhances the stimulation of plant growth by phytohormones production or by releasing beneficial organic compounds.

Beside plant growth stimulation, *Bacillus Subtilis* and its related species strain are involved in plant protection against phyto-pathogenic attacks. They act directly against pathogens by producing extracellular lytic enzyme and secondary metabolites with inhibitory growth action or interfere by quorum quenching to disturb cell-to-cell communication of the infectious expression in pathogenic bacteria. They could also compete with plant pathogen for the available nutrient and niche. Another important role is the reduction of the infection process by inducing a defense response in the host plant.

Each single microbial series is separately cultivated in its designated cultivation medium, and the optimal pH in the growing and reproduction of different microbial series also varies. Therefore, proper control and regulation of pH of the cultivation medium are provided in the course of bacterial cultivation and fermentation. The microbial series acquires energy through aerobic respiration. However, the aerobic respiration generally has to rely upon only the oxygen dissolved in the cultivation medium, i.e., the dissolved oxygen, and the containment of the dissolved oxygen in the cultivation medium is not always provided in sufficient amount and will be soonest consumed by bacteria since oxygen is difficult to get dissolved in water. Therefore, constant air supply to the microbial series is provided without interruption in the course of the cultivation and fermentation of the microbial series. Compositions of cultivation medium selected and the optimal growing environment conditions for each microbial series are detailed as follows:

When the cultivation of each microbial series is saturated in its cultivation medium, cross cultivation is followed. The compound microbial preparation differs from a single bacteria species or a single microbial product for soil modification. In some embodiments, the microbial life activities from multiple preselected microbial series are provided that are mutually coordinated and contained for crops or plants to get the results of specific fertilizers; that is, multiple microorganisms are screened from the soil and selectively bred to become capable of improving nutrition of the crops, and then to provide nitrogen, phosphor, and potassium fertilizers important to the growth of the plants in organic means by taking advantage of interaction among compound microbial preparations. Wherein, the nitrogen fixing series fixes nitrogen molecules in the nature to make it a nitrogen source for manufacturing fertilizers; the phosphoric acid releasing series unlocks and converts insolvable phosphates in the soil into phosphor, ferrous, and calcium fertilizers; the yeast group series makes it available in the making of vitamins and growing hormones, and decomposes organics to improve disease-resistant sufficiency of the plants; the photosynthetic bacteria series while being applied in manufacturing of glucose secrets carotenoid and eliminates toxic substances including hydrogen sulfide and ammonia; the actinomyces series secrets antibiotic substances at a constant amount on long-term bases to inhibit diseases; and the growing factors producing series also releases on long-term basic a given amount of growing hormones to promote roots, stalks and leaves of crops or plants to grow strong. In some embodiments, one or more of the above described series of microbials are used.

In the course of cross cultivation, each of those eight microbial series maintains intrigue symbiosis and shared prosperity among one another by playing a critical role with secretions of its own particular active organics. For example, the nitrogen fixing series converts the molecular nitrogen into ammoniac nitrogen and the resultant ammoniac nitrogen is partially to be consumed by the nitrogen fixing series, the remaining ammoniac nitrogen is synthesized into organic nitrogen to be consumed by other bacterial series; and the yeast group series may catalyze polysaccharide into simple sugar including glucose to be consumed by lactobacillus to convert into alcohol. Each microbial series supports activities of other microbial series with its synthetic proficiency while taking advantage of those substances produced by other microbial series to constitute a commonwealth circle. However, behind the big chain of food that relies on symbiosis substances, a survival game of gigantic resistance and wipe out takes place among one another due to different properties. In the environment seeing violent stimulation, new endocrines are produced. What's more important is that any strain of bacteria survived is practically the top selected one with reliable activities.

Depending on the locality, season, depth of soil, the present invention produces the proper strains of the microbial series. Those who are familiar with the art may apply on various series, e.g. *coccus, bacillus, vibrio,* or *Spirillum;* different demands of oxygen, e.g., aerobic and/or anaerobic; different environmental requirements, e.g., acidophilus, alkalophilus, psycho-, meso-, or thermophilic to come up with a locality-specific compound microbial preparation and different microbial series may be used to produce compound microbial preparations in various applications, e.g., for fertilizer, pesticide, or promotion growth of flowers and fruits.

Spores and/or colonies that enrich soils and/or provide plant biological control agents are employed in some embodiments. These include bacteria such as *Bacillus* species, e.g., *Bacillus subtilis, Bacillus cereus, Bacillus penetrans, Bacillus licheniformis,* and *Bacillus megaterium;* fungi such as *Trichoderma,* e.g., *Trichoderma hamatum, Trichoderma harzianum, Trichoderma polysporum, Trichoderma konigii, Trichoderma viride;* yeast such as *Saccharomyces cerevisiae;* and mixtures of these. Other examples are given hereafter.

To guide the evolution of each generation of microbes, microbial whole-genome sequencing can be used for mapping genomes of novel organisms, finishing genomes of known organisms, or comparing genomes across multiple samples. Sequencing the entire microbial genome is important for generating accurate reference genomes, for microbial identification, and to guide whether the current microbial generation is better than the prior generation for particular characteristics or features for farming purposes. While capillary sequencing or PCR-based system can be used, next-generation sequencing (NGS) can sequence hundreds of organisms with the power of multiplexing. Unlike traditional methods, NGS-based microbial genome sequencing doesn't rely on labor-intensive cloning steps, saving time and simplifying the workflow. NGS can identify low frequency variants and genome rearrangements that may be missed or are too expensive to identify using other methods. De novo whole-genome sequencing involves assembling a genome without the use of a genomic reference and is often used to sequence novel microbial genomes. Illumina sequencers can be used. Microbial whole-genome resequencing involves sequencing the entire genome of a bacteria, virus, or other microbe, and comparing the sequence to that of a known reference. Generating rapid and accurate microbial genome sequence information is critical for detecting low frequency mutations, finding key deletions and insertions, and discovering other genetic changes among microbial strains. A Library Preparation can be done before the sequencing and assembly. A Nextera DNA Flex Library Prep Kit or the TruSeq DNA PCR-Free Library Preparation Kits can be used. Benchtop sequencers such as the iSeq or nextSeq system can be used, or the High-Throughput Sequencing Systems such as the HiSeq 4000 System or the NovaSeq 6000 System can be used for throughput. Apps are then used for de novo assemblies or mapping of contigs and scaffolds. De novo assembly of bacteria using the Velvet assembler with a focus on Nextera Mate Pair data. An assembler performs a contig assembly, builds scaffolds, removes mate pair adapter sequences, and calculates assembly quality metrics. A Genome Assembler then assembles the microbial genome sequences. A Genome Annotation tool enables annotation of genes and coding sequences in prokaryotic genomes, from de novo assembly sequences.

Once the microbials are bred over generations to arrive at predetermined agricultural characteristics, they are mixed with humic acid, fertilizer and kelp fillers. Preferably the result is a solid or pellet that contains everything needed to be inserted into the soil to amend the soil. Humic substances are formed by the microbial degradation of dead plant matter, such as lignin and charcoal. Humic substances in the lab are very resistant to further biodegradation. The precise properties and structure of a given sample depend on the water or soil source and the specific conditions of extraction. Nevertheless, the average properties of lab produced humic substances from different sources are remarkably similar. Humic substances in soils and sediments can be divided into three main fractions: humic acids, fulvic acids, and humin. The humic and fulvic acids are extracted as a colloidal sol from soil and other solid phase sources into a strongly basic aqueous solution of sodium hydroxide or potassium hydroxide. Humic acids are precipitated from this solution by adjusting the pH to 1 with hydrochloric acid, leaving the fulvic acids in solution. This is the operational distinction between humic and fulvic acids. Humin is insoluble in dilute alkali. The alcohol-soluble portion of the humic fraction is, in general, named humic acid. So-called "gray humic acids" (GHA) are soluble in low-ionic-strength alkaline media; "brown humic acids" (BHA) are soluble in alkaline conditions independent of ionic strength; and fulvic acids (FA) are soluble independent of pH and ionic strength.

Humus in nature is produced by biodegradation of tissues from dead organisms and is thus roughly synonymous with organic matter; distinctions between the two are often not precisely and consistently made. Humic acid as traditionally produced in a laboratory is not a single acid; rather, it is a complex mixture of many different acids containing carboxyl and phenolate groups so that the mixture behaves functionally as a dibasic acid or, occasionally, as a tribasic acid. Humic acid used to amend soil is manufactured using these same well established procedures. Humic acids can form complexes with ions that are commonly found in the environment creating humic colloids. Humic acids are insoluble in water at acid pH, whereas fulvic acids are also derived from humic substances but are soluble in water across the full range of pH. Humic and fulvic acids are commonly used as a soil supplement in agriculture, and less commonly as a human nutritional supplement.[14] As a nutrition supplement, fulvic acid can be found in a liquid form as a component of mineral colloids. Fulvic acids are poly-electrolytes and are unique colloids that diffuse easily through membranes whereas all other colloids do not.

Humic substances are organic compounds that are important components of humus, the major organic fraction of soil, peat, and coal (and also a constituent of many upland streams, dystrophic lakes, and ocean water). Humic acids are organic substances extracted from soil that coagulate (form small solid pieces) when a strong-base extract is acidified, whereas fulvic acids are organic acids that remain soluble (stay dissolved) when a strong-base extract is acidified. Humic substances are high-molecular-weight macropolymers but as heterogeneous and relatively small molecular components of the soil organic matter auto-assembled in supramolecular associations and composed of a variety of compounds of biological origin and synthesized de novo by abiotic and biotic reactions in soil. It is the large molecular complexity of the soil humeome to confer to humic matter its bioactivity in soil and its role as plant growth promoter.

The kelp filler acts as a very high-quality organic fertilizer. With an N-P-K ratio of approximately 1-0-2, it is a good source of nitrogen and potassium. It also contains minerals, amino acids, and trace amounts of other micronutrients. Kelp meal is seaweed and is harvested from the ocean. Also known as sea kelp. It can be added to vegetable and flower gardens, potting mixes, and lawns. Seaweed or kelp filler, has a chelating ability and helps to release locked-up minerals in garden soil. Its high potash content aids in the formation of carbohydrates, is necessary for protein synthesis, promotes early growth, improves stem strength, and contributes to cold hardiness. As if that weren't enough, seaweed contains the hormones gibberellin and auxin, which function as growth enhancers. There are also beneficial vitamins, enzymes, and about 60 trace elements. A high alginic acid content combined with a low percentage of cellulose (the ingredient which gives land plants rigidity), causes its quick decomposition, facilitating its use as a compost accelerator. When applied to the soil, it stimulates soil bacteria, which increases fertility.

Exemplary cellulase activity exposed on Luria Bertani medium supplement with carboxyl-methyl cellulose, reveal a clear halo of CMC degradation, after two days of *Bacillus* spp. strains incubation.

In one embodiment called AGN, a natural microbial soil rejuvenation and enrichment provides microbials including enzymes, metabolites and beneficial microbial biomass that aid in building soil structure. In this embodiment, the concentration of microbes can include the following:

| | |
|---|---|
| *Bacillus amyloliquefaciens* | $5.85 \times 10^7$ cfu/ml |
| *Bacillus licheniformis* | $1.80 \times 10^7$ cfu/ml |
| *Bacillus pumilus* | $4.05 \times 10^7$ cfu/ml |
| *Bacillus subtilis* | $6.30 \times 10^7$ cfu/ml |
| *Bacillus megaterium* | $2.5 \times 10^8$ CFU/ml | and the penetrant can be water with Polyloxy-(1,2-Ethanedily), alpha-(nonylphenyl)-omega-hydroxy or Alcohol Ethoxylate.

The colony-forming unit (CFU or cfu) is a measure of viable bacterial or fungal cells. CFU measures only viable cells. For convenience the results are given as CFU/mL (colony-forming units per milliliter) for liquids, and CFU/g (colony-forming units per gram) for solids.

Humic Acid can be leonardite and water, and the penetrant can be water with Polyloxy-(1,2-Ethanedily), alpha-(nonylphenyl)-omega-hydroxy. Humic Acid provides the necessary amino acids and protein to support an active microbial population to support active and healthy plant growth.

Penetrants or non-ionic penetrants facilitate even water movement into the soil both horizontally and vertically while maintaining a very low volatility. In some embodiments, the penetrants comprises a surfactant, which can be used together with heptonic acid, alkyl polyglycoside, water soluble polyacrylamides (PAMs), and/or polysiloxane emulsion. In some embodiments, the penetrants are selected to maintain soil moisture level near to root zone of predetermined plants, prevent leaching of nutrients, or both. Other surfactants can be used in various embodiments, for example: Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like. Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like. Cationic surfactants include agents such as stearyl dimethylbenzyl ammonium chloride, stearyl trimethyl ammonium chloride, benzalkonium chloride, and laurylamine oxide; and the like.

In one embodiment, the penetrant can be about 20% alcohol ethoxylate and about 80% orange oil. The penetrant can have one or more high terpene (50% by weight or more) based oils, one or more stabilizers, one or more chelating agents, one or more preservatives, one or more acidic pH adjusters and one or more organic solvents.

Surfactants can be used. Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like. Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like. Cationic surfactants include agents such as stearyl dimethylbenzyl ammonium chloride, stearyl trimethyl ammonium chloride, benzalkonium chloride, and laurylamine oxide; and the like. Amphoteric surfactants such as alkylaminoethyl glycine chloride and lecithin; and the like.

To deploy, field persons mix AGN with clean water and let it set for a minimum of 1 hour or maximum overnight (keep air flows after mixed with water) and apply directly to moist soil as a pre-plant, post-plant or seasonal treatment. The solution can be applied to soil, seeds, and plants. In some embodiments, the solution is not mixed with any other fertilizers or fungicides and deployment of such chemicals should wait at least 72 hours before or after treatment.

For tank mixing, in one embodiment, field personnel can mix 1 gallon (4 quarts or 3.8 liters) of AGN with minimum 100 gallons up to 1000 gallons of clean water in a clean tank and free of chemical. The solution can be applied at a rate of 2 to 4 quarts per surface acre or 4 to 8 liters per surface hectare.

For injection irrigation or fertigation, after tank mixing, AGN can be applied by dosage rate of 0.5 to 1 gallon (2 to 4 quarts) per surface acre (4 to 8 liters per surface hectare). For side-dress or starter, the solution can be applied at a rate of 1 to 2 quarts per surface acre or 2 to 4 liters per surface hectare. Preferably, the solution can be dispensed with:

Localized Drip or Trickle

Sprinkler, or

Contour Furrows

AGN includes Advanced Microbes for Soil Rejuvenation and creates a balanced soil environment for healthy plant growth which requires the ability to fully access the soil particulates and enriching them with phytonutrients utilizing highly concentrated microorganisms and organic materials.

The application of AGN creates superior root systems which can efficiently assimilate nutrients and micronutrients in the soil, resulting in higher yields and better plant health for all types of plants, crops, and trees and increases yields, soil-root-plant health, balance soil nutrients, penetrate and loosen clay soils, leach salts from root zones, reduce harmful nematodes, increase nutrient and micronutrient uptake as well as increase cathode ion transfer.

Any microbial spores and/or colonies can be preserved using methods and solutions of some embodiments. Spores and/or colonies of beneficial soil and plant pathogen biological control microorganisms are preferred. Microorganisms that grow rapidly and colonize substrata in soil after treatment with compositions of the invention are particularly preferred. These include, but are not limited to bacteria, e.g., *Bacillus species* such as *Bacillus subtilis, Bacillus cereus, Bacillus penetrans, Bacillus licheniformis*, and *Bacillus megaterium*; fungi, e.g., *Trichoderma species* such as *Trichoderma hamatum, Trichoderma harzianum, Trichoderma polysporum, Trichoderma konigii*, and *Trichoderma viride*; and yeast species such as *Saccharomyces cerevisiae*. As illustrated below, mixtures of microorganisms can also be preserved, and are preferred in many embodiments. Examples are given hereafter.

In the practice of the system, spores or whole microorganisms, including harvested and/or lyophilized microbial colonies containing spores, are added to solutions. The solutions can be formulated for any use requiring viable microbial spores and/or colonies such as for fertilizers, composting, food products, and pharmaceutical compositions. Liquid fertilizers are preferred for soil enrichment purposes. Water miscible dry powders and/or granules such as lyophilized preparations of spores and/or colonies are preferred in many embodiments. The amount of spores or microorganisms added to solutions of the invention is not fixed per se, and necessarily is dependent upon the degree of soil and/or plant remediation required, the number and identity of microorganism species needed in the formulation, and the concentration of other ingredients in the formulation. Preferred embodiments employ spores and/or colonies in amounts effective to achieve recolonization of the soil by spray application of the composition. Typical embodiments contain sufficient spores and/or colonies to deliver from about 1000 to about 1,000,000 colony forming units (CFU) per square foot when the preparation is delivered.

Preservative solutions of some embodiments are colloidal in nature, containing humic acid and/or other organic macromolecules. By "colloidal" is meant a state of matter which comprises either large molecules, aggregations of smaller molecules, or a combination of the two. Some embodiments contain large molecules such as humic acid and/or methylene urea compounds of varying chain length. The particles are surrounded by different matter such that a dispersed phase is surrounded by an external phase. Both phases may be solid or liquid (and sometimes gaseous). One phase comprises water in most embodiments; typical ranges are from about 35% to about 58% by weight water in the total composition, but some embodiments contain less than about 20% by weight water in the total composition.

Microorganisms and/or their spores which can be preserved using formulations of the invention further exhibit a number of desirable characteristics related to soil enrichment and improvement of soil quality described above, such as biological control of plant pathogens (already mentioned); enhancement and/or production of desirable phtyohormones, e.g., auxins, giberillins and cytokinins; and solubilization of phosphates. Certain strains of *Bacillus subtilis*, for example, inhibit *N. Galligena* that colonize apple branch scars if applied to trees after leaf fall. *E. herbicola* and *Pseudomonas* isolates have been shown to partially control fire blight of pome fruit trees. Several *Bacillus* species produce antibiotics useful when sprayed as a leaf or needle application on tobacco, Douglas fir, and apple trees, and the natural protection of leaves provided by the buffering capacity of phylloplane microorganisms has been demonstrated. *Azobacter, Rhizobium, Bacillus, Klebsiella, Azospirillium, Enterobacter, Serratia, Agrobacterium, Arthrobacter, Aerobacter, Actinomyces, Bacillus, Pseudomonas*, and other bacteria stimulate growth, increase yield, and produce other positive results by various mechanisms including enhancing nutrient uptake, increasing germination, enhancing seedling emergence, stimulating de novo biosynthesis, and the like, when applied to fields of various food plants.

The resulting solutions supply carbon-rich organic materials in a bioavailable form for soils and plants together with nutrients that feed the microorganisms as they multiply after application. Solutions of some embodiments provide an excellent food source for the germination of spores and/or colonies when the solutions are applied to soil or water. It is a further advantage that preferred solutions contain a wide variety of naturally occurring metabolites that can be readily absorbed by the growing microorganisms and enhance seed germination, root development, and growth of plants in the soil.

As summarized above, some embodiments are formulated with microorganism spores and/or cultures useful in the prevention, control and/or cure of plant diseases, particularly those of fungal origin. Illustrative examples are provided hereafter. One embodiment, for example, maintains the viability of Bacillus subtilis GB03 (EPA Reg. No. 7501-144), a bacteria recognized to colonize developing root systems, suppressing disease organisms such as *Fusarium, Rhizoctonia, Alternaria* and *Aspergillus* that attack root systems. Compositions of the invention can be used to treat developed root systems as well as developing root systems. As the root system develops, grows, and functions, the bacteria grow with the roots, extending protection throughout the growing season. As a result of this biological protection, a vigorous root system can be established and maintained by the plants.

In addition, *B. subtilis* GB03 has been shown to increase the amount of nodulation by nitrogen-fixing bacteria when used on many legumes. This improvement in nodulation is a result of a healthier root system, allowing more sites for nodules to form from naturally-occurring soil borne nitrogen-fixing bacteria. Illustrative examples follow.

Soil bacteria in the genus *Bacillus* are well known for contributions to improving soil structure, nutrient availability and as a competitive excluder to harmful pathogens. *Bacillus lichniformis* produces a variety of extracellular enzymes that are associated with the cycling of nutrients in nature, thus improve nutrient availability and nutrient uptake. *Bacillus pumilus* is an agricultural fungicide. Growth of the bacterium on plant roots prevents rhizoctonia and fusarium spores from germinating. These strains are heavily involved with inhibition of opportunistic pathogens as well as improving nutrient availability and nutrient uptake. *Bacillus subtilis* does nitrogen fixing; produce inhibitory compounds that reduce the growth of harmful microorganism. It interfere with the germination of plant pathogen spores and their attachment to host plants, acts as a prebiotic conditioning plants own defense mechanisms prior to attack from potential pathogens. *Bacillus amyloliquefaciens* had anti fungal properties and help nitrogen fixing availability. *Bacillius megaterium* is a plant growth-promoting rhizobacteria (PGPR) and phosphate solubilizing. It promotes the activation of plant defense responses and secretion of plant growth-regulating substances such as auxins, cytokinins and bacterial volatiles. Phytohormones are involved in the control of growth and in almost every important developmental process in plants. Bacterial secretion of phytohormones can impact root architecture by overproduction of root hairs and lateral roots and subsequently increased nutrient and water uptake, thus contributing to growth.

In some examples, the method to provide plant nutrient includes selecting a microbial solution with predetermined characteristics for agriculture use; iteratively and selectively breeding generations of microbes for microbial strain selection with predetermined microbial gene profiles to arrive at a predetermined microbial solution, wherein multiple single microbial series are separately cultivated and followed with cross cultivation among the microbial series in a specific sequence.

EXAMPLE 1 (AGN)

Microbes:
*Bacillus amyloliquefaciens* at $5.0 \times 10^7$ cfu/ml
*Bacillus licheniformis* at $1.0 \times 10^8$ cfu/ml
*Bacillus subtilis* at $5.0 \times 10^7$ cfu/ml
*Bacillus megaterium* $1.0 \times 10^8$ CFU/ml
Humic Acid: Leonardite and H2O
Nitrogen: Urea and H2O
Penetrant: Polyloxy-(1,2-Ethanedily), Alpha-(nonylphenyl)-omega-hydroxy and H2O

Example 2 (AGN LTE)

*Bacillus amyloliquefaciens* at $7.5 \times 10^8$ cfu/ml
*Bacillus licheniformis* at $7.5 \times 10^7$ cfu/ml
*Bacillus megaterium* $2.5 \times 10^8$ CFU/ml
*Bacillus subtilis* at $1.0 \times 10^8$ cfu/ml
Humic Acid: Leonardite and H2O In other examples, the method includes iteratively and selectively breeding generations of microbes for microbial strain selection with predetermined microbial gene profiles to arrive at a predetermined microbial solution wherein multiple single microbial series are separately cultivated and followed with cross cultivation among the microbial series in a specific sequence; and mixing by-products produced by the crossly cultivated microbial series with a soil amendment or nutrient. Such soil amendment or nutrient can be fertilizer, mineral, or a combination of both.

The above description is for the purpose of illustrating and not limiting the present invention, and teaching the person of ordinary skill in the art how to practice the invention. It is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The patents, papers, and book excerpts cited above are hereby incorporated herein by reference in in their entireties.

What is claimed is:

1. A method for enhancing soil in a predetermined farming area, comprising:
   selecting a plurality of strains of sporulated living *Bacillus* species to form a microbial solution comprising:
   iteratively and selectively breeding generations of the *Bacillus* species for strain selection having predetermined microbial gene profiles, and forming said microbial solution in a concentrated form, wherein multiple *Bacillus* species are separately cultivated and followed with cross cultivation in a specific sequence;

selecting a carrier for a predetermined animal as follows:

for grazing animal, one of hull, wheat, and dendritic salt, for poultry, dendritic salt or calcium carbonate, for aquatic animal, dendritic salt, and for swine, dendritic salt or calcium carbonate;

applying said microbial solution to the carrier to provide a microbial infused carrier;

performing feed blending between 0.01 to 1 gram of said microbial infused carrier per kg of feed as a pre-mixed feed or feed coating for feeding said predetermined animal;

feeding said predetermined animal with the blended feed comprising said microbial infused carrier:

excrementing the miriboal infused carrier as the predetermined animal moves around the farming area to release the microbial infused carrier into soil of the predetermined farming area; and activating the *Bacillus* strains of said microbial infused carrier using an aqueous liquid for enhancing the soil.

2. The method of claim 1, comprising feeding the predetermined animal with said microbial infused carrier to deliver the *Bacillus* strains into a gastrointestinal tract alive.

3. The method of claim 2, comprising germinating the *Bacillus* strains in a digestive tract and stimulating local intestinal immunity with the *Bacillus* strains.

4. The method of claim 1, comprising selecting the *Bacillus* species from *Bacillus* (*B.*) *acidiceler, B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a. subsp. amyloliquefaciens, B. a. subsp. plantarum, B. amylolyticus, B. andreesenii, B. aneurinilyticus, B. anthracis, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g. subsp. globisporus, B. g. subsp. marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s. subsp. inaquosorum, B. s. subsp. spizizenii, B. s. subsp. subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis,* and *B. zhanjiangensis.*

5. The method of claim 1, comprising germinating in an upper digestive tract of said predetermined animal and acting on predetermined sections of an intestine for nutrient absorption.

6. The method of claim 1, wherein the hull comprises corn or almond hull.

\* \* \* \* \*